US008965710B2

(12) United States Patent
Ligler et al.

(10) Patent No.: US 8,965,710 B2
(45) Date of Patent: Feb. 24, 2015

(54) AUTOMATED SAMPLE-TO-MICROARRAY APPARATUS AND METHOD

(75) Inventors: Frances S Ligler, Potomac, MD (US); David A Stenger, Herndon, VA (US); Jeff Erickson, Bethesda, MD (US); Marie Archer, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1447 days.

(21) Appl. No.: 11/559,513

(22) Filed: Nov. 14, 2006

(65) Prior Publication Data

US 2007/0092901 A1    Apr. 26, 2007

Related U.S. Application Data

(63) Continuation-in-part of application No. 11/177,647, filed on Jul. 2, 2005, now Pat. No. 8,032,310, and a continuation-in-part of application No. 11/177,646, filed on Jul. 2, 2005, now abandoned, and a continuation-in-part of application No. 11/268,373, filed on Nov. 7, 2005, now abandoned, and a continuation-in-part of application No. 11/422,425, filed on Jun. 6, 2006, now Pat. No. 7,695,941, which is a continuation-in-part of application No. 11/177,647, filed on Jul. 2, 2005, now Pat. No. 8,032,310, and a continuation-in-part of application No. 11/177,646, and a continuation-in-part of application No. 11/268,373, application No. 11/559,513, which is a continuation-in-part of application No. 11/422,431, filed on Jun. 6, 2006, now Pat. No. 7,623,997, which is a continuation-in-part of application No. 11/177,647, said application No. 11/422,431 is a continuation-in-part of application No. 11/177,646, said application No. 11/422,431 is a continuation-in-part of application No. 11/268,373.

(60) Provisional application No. 60/691,768, filed on Jun. 16, 2005, provisional application No. 60/735,876, filed on Nov. 14, 2005, provisional application No. 60/735,824, filed on Nov. 14, 2005, provisional application No. 60/743,639, filed on Mar. 22, 2006, provisional application No. 60/609,918, filed on Sep. 15, 2004, provisional application No. 60/631,460, filed on Nov. 29, 2004, provisional application No. 60/590,931, filed on Jul. 2, 2004, provisional application No. 60/631,437, filed on Nov. 29, 2004, provisional application No. 60/626,500, filed on Nov. 5, 2004.

(51) Int. Cl.
*G06F 19/20* (2011.01)
*C12Q 1/68* (2006.01)
*C12M 1/34* (2006.01)
*B01L 3/00* (2006.01)
*B01L 7/00* (2006.01)
*G01N 35/00* (2006.01)

(52) U.S. Cl.
CPC .................. *B01L 3/5027* (2013.01); *B01L 7/52* (2013.01); *B01L 2200/10* (2013.01); *B01L 2300/0636* (2013.01); *B01L 2300/087* (2013.01); *B01L 2300/1827* (2013.01); *B01L 2400/0481* (2013.01); *B01L 2400/0487* (2013.01); *G01N 2035/00158* (2013.01)
USPC ........................... 702/20; 435/6.1; 435/287.2

(58) Field of Classification Search
None
See application file for complete search history.

(56) References Cited

U.S. PATENT DOCUMENTS

| 5,856,174 A | 1/1999 | Lipshutz et al. |
| 6,040,138 A | 3/2000 | Lockhart et al. |
| 2002/0022261 A1* | 2/2002 | Anderson et al. .......... 435/287.2 |
| 2003/0143571 A1* | 7/2003 | Sharp et al. ...................... 435/6 |

OTHER PUBLICATIONS

Liu et al., "Self-Contained, Fully Integrated Biochip for Sample Preparation, Polymerase Chain Reaction Amplification, and DNA Microarray Detection", 2004, Analytical Chemistry, vol. 76, pp. 1824-1831.*
Goei et al. Isolation of Novel Non-HLA Gene Fragments from the Hemochromatosis region (6p21.3) by cDNA Hybridization Selection. American Journal of Human Genetics vol. 54, pp. 244-251 (1994).*
PCT search report and written opinion in corresponding PCT application.
Anderson et al., "A minature integrated device for automated multistep genetic assays" *Nucleic Acids Research*, 28(12), e60 (2000).

(Continued)

*Primary Examiner* — John S Brusca
(74) *Attorney, Agent, or Firm* — US Naval Research Laboratory; Joseph T. Grunkemeyer

(57) ABSTRACT

An apparatus having within or as part of a housing; a sample port; a microarray port; a lysis module; a purification module for containing a solid phase for binding of oligonucleotides; a thermocycling module for containing a polymerase chain reaction; a fragmentation module; and a microarray module for holding a microarray and a liquid in contact with the microarray. The apparatus is configured to be coupled to a device for: pumping a liquid through, in order, the lysis, purification, thermocycling, fragmentation, and microarray modules; sonicating any contents of the lysis module; thermocycling the thermocycling module to perform the polymerase chain reaction; heating the fragmentation module to fragment any oligonucleotides contained therein; circulating a fluid over the surface of the microarray; and performing one or more washing or staining steps on the microarray.

12 Claims, 5 Drawing Sheets

(56) References Cited

OTHER PUBLICATIONS

Bavykin et al., "Portable System for Microbial Sample Preparation and Oligonucleotide Microarray Analysis" *Appl. Environ. Microbiol.*, 67(2), 922-928 (2001).

Bruckner-Lea et al., "Renewable microcolumns for automated DNA purification and flow-through amplification: from sediment samples through polymerase chain reaction" *Analytica Chimica Acta*, 469, 129-140 (2002).

Hong et al., "A nanoliter-scale nucleic acid processor with parallel architecture" *Nature Biotechnology*, 22(4), 435-439 (2004).

Lee et al., "Microchip-based one step DNA extraction and real-time PCR in one chamber for rapid pathogen identification" *Lab on a Chip*, 6, 886-895 (2006).

Legendre et al., "A Simple, Valveless Microfluidic Sample Preparation Device for Extraction and Amplification of DNA from Nanoliter-Volume Samples" *Anal. Chem.*, 78, 1444-1451 (2006).

McMillan et al., "Application of advanced microfluidics and rapid PCR to analysis of microbial targets" Microbial Ecology in Industry, Microbial Biosystems: New Frontiers, Proceedings of the 8th International Symposium on Microbial Ecology, Halifax, Canada (1999).

Millar et al., "Solid-Phase Hybridization Capture of Low-Abundance Target DNA Sequences: Applications to the Polymerase Chain Reaction Detection of *Mycobacterium paratuberculosis* and *Mycobacterium avium* subsp. *silvaticum*" *Anal. Biochem.*, 226, 325-330 (1995).

Pradel et al., "Genomic Subtraction to Identify and Characterize Sequences of Shiga Toxin-Producing *Escherichia coli* O91:H21" *Appl. Environ. Mlicrobiol.*, 68(5), 2316-2325 (2002).

Raja et al., "Technology for Automated, Rapid, and Quantitative PCR or Reverse Transcription-PCR Clinical Testing" *Clinical Chem.*, 51(5) 882-890 (2005).

Schilling et al., "Cell Lysis and Protein Extraction in a Microfluidic Device with Detection by a Fluorogenic Enzyme Assay" *Anal. Chem.*, 74(8), 1798-1804 (2002).

Waters et al., "Microchip Device for Cell Lysis, Multiplex PCR Amplification, and Electrophoretic Sizing" *Anal. Chem.*, 70, 158-162 (1998).

Wilding et al., "Integrated Cell Isolation and Polymerase Chain Reaction Analysis Using Silicon Microfilter Chambers" *Anal. Biochem.*, 257, 95-100 (1998).

Yang et al., "An integrated, stacked microlaboratory for biological agent detection with DNA and immunoassays" Biosensors and Bioelectronics, 17, 605-618 (2002).

Yuen et al., "Microchip Module for Blood Sample Preparation and Nucleic Acid Amplification Reactions" *Genome Research*, 11, 405-412 (2001).

* cited by examiner

AUTOMATED SAMPLE-TO-MICROARRAY APPARATUS AND METHOD

This application claims priority to U.S. Provisional Patent Application Nos. 60/735,876 filed on Nov. 14, 2005; 60/735,824 filed on Nov. 14, 2005; and 60/743,639, filed on Mar. 22, 2006, all incorporated herein by reference. This application is a continuation-in-part application of U.S. patent application Ser. No. 11/177,647, filed Jul. 2, 2005; Ser. No. 11/177,646, filed Jul. 2, 2005; Ser. No. 11/268,373, filed on Nov. 7, 2005; Ser. No. 11/422,425, filed on Jun. 6, 2006; and Ser. No. 11/422,431, filed on Jun. 6, 2006, all incorporated herein by reference. These nonprovisional applications claim priority to U.S. Provisional Patent Application Nos. 60/590,931, filed on Jul. 2, 2004; 60/609,918, filed on Sep. 15, 2004; 60/626,500, filed on Nov. 5, 2004; 60/631,437, filed on Nov. 29, 2004; 60/631,460, filed on Nov. 29, 2004; and 60/691,768, filed on Jun. 16, 2005, all incorporated herein by reference.

FIELD OF THE INVENTION

The invention is generally related to biological sample processing and identification.

DESCRIPTION OF RELATED ART

Frequently, there is no unique correspondence between a set of clinical symptoms and a specific pathogen. Respiratory symptoms and fever, in particular, can be caused by a wide variety of bacteria and viruses. Multiplexed assays based on DNA arrays are particularly well suited for discriminating among the multitude of pathogens. In addition to naturally occurring pathogens, bioterrorism adds the threat from unexpected pathogens which can masquerade as a common respiratory infection. Surveillance for bioterrorist agents during routine medical diagnostic procedures at an affordable per-assay cost remains an elusive goal. The time, operator skill, and cost required to perform the assays generally parallels the amount and quality of the information obtained.

Nucleic acid microarrays can detect pathogens at the genetic level and offer the potential for broad-spectrum surveillance, diagnostics, and for the investigation of gene expression within a species. Multiple pathogens can be identified at the strain level directly from clinical fluids (Lin et al., *Genome Res.* 16, 527-535 (2006). All referenced publications and patent documents are incorporated herein by reference.). High density nucleic acid microarrays can have hundreds of thousands of spots, so that the number of pathogens possible to detect becomes limited by the ability to perform generic or highly multiplexed PCR amplifications. In addition, nucleic acid microarrays have demonstrated higher sensitivity than traditional antibody-based assays, making the detection of pathogens down to 10 cfu/mL or 10 pfu/mL possible. Indeed, several studies have shown the utility of DNA microarrays for pathogen detection (Call et al., *Antimicrob. Agents Chemother.* 47, 3290-3295 (2003); Call et al., *J. Microbiol. Methods* 53, 235-243 (2003); Chizhikov et al., *Appl. Environ. Microbiol.* 67, 3258-3263 (2001); Chizhikov et al., *J. Clin. Microbiol.* 40, 2398-2407 (2002); Davignon et al., *J. Clin. Microbiol.* 43, 5690-5695 (2005); Gingeras et al., *Genome Res.* 8, 435-448 (1998); Lin et al., *Genome Res.* 16, 527-535 (2006); Roth et al., *J. Clin. Microbiol.* 42, 4268-4274 (2004); Troesch et al., *J. Clin. Microbiol.* 37, 49-55 (1999); Wang et al., *Proc. Natl. Acad. Sci. USA* 99, 15687-15692 (2002); Wang et al., *PLoS Biol.* 1, E2 (2003); Wang et al., *Emerg. Infect. Dis.* 12, 638-646 (2006); Wilson et al., *Appl. Environ. Microbiol.* 68, 2535-2541 (2002); Wilson et al., *Mol. Cell Probes* 16, 119-127 (2002)).

Microarray technology can require costly and cumbersome equipment to perform assays and significant technical expertise from the operators. In order to move microarray technology from the lab to the point-of-care, conversion of the bulky benchtop devices to portable, automated systems is the key. To integrate the microarray and sample processing systems, one or more hurdles may need to be overcome. These may include, but are not limited to, the processes of automating (1) cell lysis and nucleic acid extraction, (2) reverse transcriptase (if desired) and polymerase amplification, (3) fragmentation and biotinylation (if desired) (4) hybridization (5) washing and staining, (6) reading the image, and (7) interpreting the data.

In 2000, a microfluidic device the size of a credit card was demonstrated for the processing of Affymetrix GeneChips (Anderson et al., *Nucleic Acids Res.* 28, e60 (2000)). The conditions under which the automated hybridization and staining operations were performed were designed for a very specific HIV analysis. The demonstrated hybridization took place at only 37° C. and for only 20 minutes; it would need to be modified and tested for broad spectrum diagnostic applications. Furthermore, the device was designed around GeneChips that were removed from their protective housing. Handling exposed GeneChips in the field can be difficult, especially when transferring them outside of the device between the hybridization and scanning steps.

More recently, a microfluidic device was designed for use with CombiMatrix microarrays (Liu et al., *Anal. Chem.* 78, 1980-1986 (2006)). This device contained electrochemical pumps, mixers, and reagent chambers; provided on-chip electrodes which could be used to move target DNA toward probe DNA; and was small enough to be hand-held. The automated hybridization, washing, and staining steps were not suitable for the point-of-care diagnostic applications for a number of reasons. First, the hybridization demonstrated by Liu et al. required 18 hours, which is far too long for rapid diagnostics. Furthermore, significant evaporative losses were incurred by the mixing process used in this device, resulting in the loss of hybridization stringency and requiring the use of a high humidity atmosphere to minimize losses. Finally, the feature size of the CombiMatrix chips is limited, and they do not possess the re-sequencing capabilities that other commercial platforms do. Clearly, a need still exists for automated systems to move microarray technology from the lab to the point-of-care.

A number of prior studies have attempted to incorporate sample lysing, nucleic acid purification, or both into automated devices for nucleic acid analysis. Waters and co-workers developed a microfluidic device capable of performing thermal cell lysis, multiplexed PCR amplification, and gel electrophoresis (Waters et al., *Anal. Chem.*, 70, 158-162 (1998)). The device was demonstrated on whole *E. coli* cells that were suspended in a water/PCR buffer mix, but no nucleic acid purification step was performed prior to the PCR amplification. Yuen and co-workers demonstrated a module for the separation of white blood cells from whole blood using a wier-type filter, followed by a thermal lysing step and PCR (also no purification step) (Yuen et al., *Genome Research*, 11, 405-412 (2001)). Devices such as these are effective for cells spiked into buffers, and for very specific types of samples. However, due to the presence of PCR inhibitors in a wide variety of samples and chemicals used for lysing, an optimal device would also employ a nucleic acid purification step. Legendre and co-workers demonstrated a device which accepted a manually-lysed sample and performed automated solid phase extraction on a silica bead sol/gel column, followed by on-chip PCR (Legendre et al., *Anal. Chem.*, 78, 1444-1451 (2006)). Anderson and co-workers describe a microfluidic device smaller than a credit card that is capable of performing a nucleic acid purification on DNA clones spiked into fetal bovine serum using columns packed with secondary associated fibril cellulose, performing a PCR amplification, and hybridizing the products to a nucleic acid microarray (Anderson et al., *Nucleic Acids Research*, 28, e60 (2000)). The device did not contain a unit for sample lysing; rather that step was performed manually by the user. While useful, an optimal field-portable device would contain both automated sample lysing as well as nucleic acid purification. Hong and co-workers demonstrated an automated device fabricated by soft lithography for the lysing of small numbers of cells, followed by bead-based solid phase extraction (Hong et al., *Nature Biotechnology*, 22, 435-439 (2004)). They demonstrated that their device was suitable for the recovery of both DNA and mRNA. However, this device did not perform any downstream operations such as PCR or analysis. Lee and co-workers demonstrated a microfluidic device that lysed both gram-negative and gram-positive bacteria using a laser-irradiated magnetic bead system (Lee et al., *Lab on a Chip*, 6, 886-895 (2006)). The carboxyl-terminated magnetic beads also served to clean the sample by binding and removing denatured proteins before on-chip real-time PCR operations were performed.

SUMMARY OF THE INVENTION

The invention comprises an apparatus comprising: a housing; a sample port for placing a liquid biological sample into the housing; a microarray port for inserting an oligonucleotide microarray into the housing; a lysis module within the housing and coupled to the sample port; a purification module within the housing coupled to the lysis module and capable of containing a solid phase for binding of oligonucleotides; a thermocycling module within the housing coupled to the purification module and capable of containing a polymerase chain reaction; a fragmentation module within the housing coupled to the thermocycling module; and a microarray module within the housing coupled to the fragmentation module and capable of holding the microarray and a liquid in contact with the microarray. The apparatus is configured to be coupled to a device capable of: pumping a liquid through, in order, the lysis module, the purification module, the thermocycling module, the fragmentation module, and the microarray module; sonicating any contents of the lysis module; thermocycling the thermocycling module to perform the polymerase chain reaction; heating the fragmentation module to fragment any oligonucleotides contained therein; circulating a fluid over the surface of the microarray; and performing one or more washing or staining steps on the micro array.

The invention further comprises a method comprising: providing the above apparatus; inserting an oligonucleotide microarray into the microarray port; inserting the sample through the sample port and into the lysis module; and coupling the apparatus to a device, the device performing a process comprising: sonicating the sample in the lysis module; pumping the product of the sonicating into the purification module; binding oligonucleotides to the solid phase; eluting the bound oligonucleotides to the thermocycling module; introducing a set of PCR primers into the thermocycling module; performing a polymerase chain reaction within the thermocycling module; pumping the product of the polymerase chain reaction into the fragmentation module; introducing a restriction enzyme into the fragmentation module; heating the contents of the fragmentation module to cause fragmentation of the oligonucleotides; pumping the product of the fragmentation into the microarray module; circulating the product of the fragmentation over the microarray to allow hybridization of oligonucleotides to the microarray; and performing one or more washing or staining steps on the hybridized microarray.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Disclosed herein is an automated system to process a complex sample through production of a DNA microarray for genetic analysis of one or more targets. Also disclosed is a protocol that may include some or all of the following processes: cell lysis, nucleic acid extraction, subtraction of host oligonucleotides or enrichment of target oligonucleotides, reverse transcriptase, DNA amplification, amplicon fragmentation and labeling, hybridization to a DNA microarray, and staining.

The system may be a robust and automated sample preparation system which includes effective target concentration and purification, amplification, and hybridization to gene arrays with multiplex capability. Such a system may provide: more extensive multiplex capability than is possible with real-time PCR; more reliable identification than real-time PCR in terms of the specificity of the signal generated; reduction in manpower costs and operational time for future validation of clinical or environmental assays; and the potential for resequencing pathogen genes (provided by Affymetrix gene arrays), which provides a high level of confidence in terms of zero false positives and identification of near neighbors. The same system could be used with spotted microarrays in order to simplify the processing, reduce the hybridization and staining times, reduce the opportunity for sample cross contamination, and lower the cost.

The system may satisfy several criteria. First, it may be rapid and sensitive enough to be used with clinical samples in a standard diagnostic environment (as opposed to a research laboratory), yet flexible enough to be able to detect a wide variety of common pathogens and bio-warfare agents. Secondly, the device may have a reasonable per-assay cost; it would be used where broad-spectrum, high sensitivity biosurveillance capability is critical with a view toward testing one sample for many (e.g. 20-100) pathogens in 3-10 hours rather than a quick diagnostic test for a single pathogen. Third, the device may be fully automated, require little operator expertise, and have few or no sample preparation steps performed by a technician other than inserting the sample into the device. Fourth, in order to avoid cross contamination, the device may be made from disposable and interchangeable parts and each sample should be retained in a fully enclosed package throughout the process.

Figure 1:
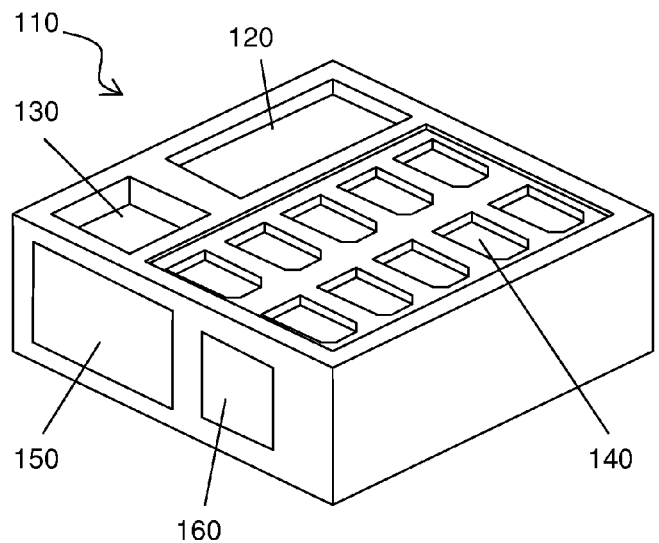
FIG. 1 schematically illustrates an embodiment of a controlling device.
Figure 2:
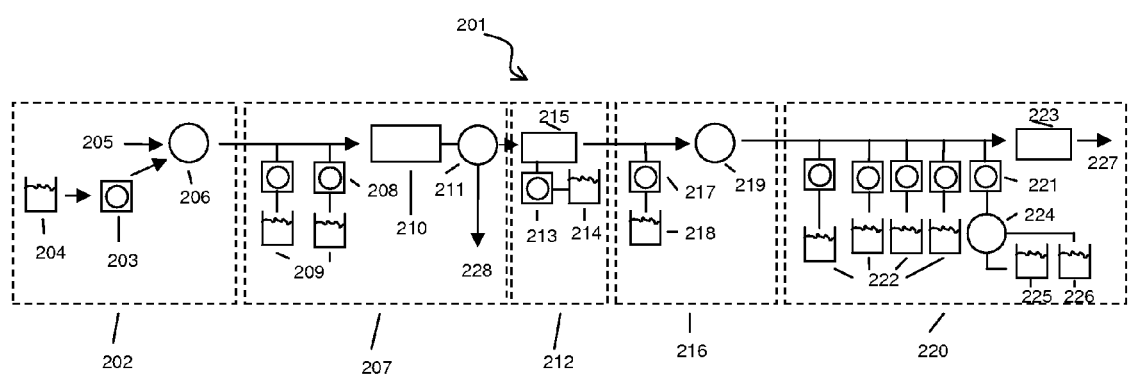
FIG. 2 schematically illustrates an embodiment of a disposable cartridge coupled to a controlling device.

Schematics of embodiments of an integrated device are shown in FIGS. 1 and 2. FIG. 1 shows the device 110 to which multiple disposable parts can be coupled. The disposable parts may be placed in the housing for sample processing devices 120, housing for reagents cassette 130, and housing for microarray chambers 140. The sample processing devices, reagents cassette, and microarray chambers (not shown) may together make up the apparatus. The illustrated device includes a display screen 150 and operator controls 160. FIG. 2 schematically illustrates an apparatus 201 having a component for lysing 202, and component for extraction 207, a component for RT-PCR and PCR 212, a component for labeling 216, and a component for hybridizing, washing, and staining 220. Pump 203 pumps lysing buffer from a reservoir 204 into a lysing chamber 206. Injected sample 205 also enters lysing chamber 206. The output of the lysing chamber 206 moves into an extraction chamber 210. Pumps 208 pump washing buffer and elution buffer from reservoirs 209 into the extraction chamber 210. The output of the extraction chamber moves through valve 211 into either waste 228 or into thermocycling chamber 215. Pump 213 pumps PCR reagents from reservoir 214 into thermocycling chamber 215. The output of thermocycling chamber 215 moves into fragmentation and labeling chamber 219. Pump 211 pumps fragmentation and labeling solutions from reservoir 218 into fragmentation and labeling chamber 219. The output of fragmentation and labeling chamber 219 moves into wash/stain/hybridize chamber 223, which contains the microarray. Pumps 221 pump hybridization buffer and wash/stain solutions from reservoirs 221 into wash/stain/hybridize chamber 223. Solutions from some reservoirs 225, 226 pass through valve 224. The output of wash/stain/hybridize chamber 223 is waste 227. The device can be fabricated to process a single sample to produce a single microarray chip to one that processes multiple samples simultaneously to produce multiple chips. Aqueous samples (e.g. nasal washes, serum, swab eluates, ground water, effluent from air samplers) are injected directly into the first module of the device. The first module adds buffers including nuclease inhibitors and performs a lysis step to release the nucleic acids from the cells, bacteria, viruses, and spores in the sample. (There is no requirement of a one-to-one correspondence between "modules" as recited in the attached claims and "chambers" described in the embodiments. A module may include one or more chambers, the functions of a module may occur in one or more chambers, and/or the functions of more than one module may take place in one chamber. For example, the lysis and purification modules may share a single chamber and/or the fragmentation and thermocycling modules may share a single chamber.) The second module nonspecifically extracts the nucleic acids in the sample and resuspends them into a PCR-compatible buffer. The third module performs an automated reverse transcriptase reaction and multiplexed nucleic acid amplification. A selective solid phase for subtraction or enrichment may or may not be included prior to or after the reverse transcriptase procedure, depending on the process requirements for device operation. In the fourth module, the amplified sample is fragmented and end-labeled (if desired) in preparation for hybridization. Finally, the fifth module hybridizes, stains, and washes the gene chip, such as an Affymetrix resequencing chip. After hybridization, the gene-chip is manually removed from the device and placed in a separate, automated chip-reader for scanning. The entire process, from sample injection to chip-reading, may require less than 9 hours, depending on whether multiplexed or random amplification is used. When used with spotted DNA arrays, the protocol may be somewhat simpler and significantly faster.

Lysis Module

In most samples, it is necessary to lyse cells, bacteria, viruses and spores before the genetic material can be isolated. The automation of these lysing procedures is an important development in diagnostic and surveillance activities, because it prevents cross contamination between samples as well as minimizes the amount of technical expertise required of the operator. Automation also eliminates time-consuming manual steps in most processes.

There are a large number of lysis methods that have been explored in the literature. Depending on the downstream process, some techniques will not be applicable. For example, lysozyme is a known PCR inhibitor and rupturing cells by adding this enzyme to solution can cause problems in downstream amplification procedures, even if the enzyme is denatured prior to PCR. Furthermore, although most lysing techniques are useful with simple pathogenic bacteria, only a few are amenable to the rupture of spores such as *Bacillus Anthracis*. For these reasons, sonication is used, with or without the addition of beads. The beads or any other lysis reagent may be stored in a lysis reagent reservoir coupled to the lysis chamber.

*E. coli* bacteria and *B. Globigii* spores were used as model pathogens in the preliminary work. *E. coli* bacterial cultures were grown and stored in stocks of approximately $1 \times 10^9$ cfu/mL at 4° C. in LB broth for no more than 10 days or until use. The cells were diluted to $1 \times 10^5$ cfu/mL immediately before use in experiments. After sonication, the cells were plated out onto LB Agar at 1000 colonies per plate and allowed to incubate for at least 12 hours at 30° C.

*B. Globigii* spores were obtained as dry stock. The spores were diluted in DI water at approximately $1 \times 10^9$ cfu/mL, and stored at 4° C. until use. The cells were diluted to $1 \times 10^4$ cfu/mL immediately before use in experiments. After sonication, the cells were plated out onto standard plate count agar at 1000 colonies per plate and allowed to incubate for at least 18 hours at 37° C.

Sonication took place under two separate geometries. In the probe configuration, a long metal probe was attached to a 400 W (maximum power) Branson Sonifier ultrasonic horn and was inserted directly into the sample. The samples were placed into 15 mL Falcon tubes, which were suspended in a cooling bath to prevent excess heat buildup. In the bath configuration, samples were placed into either 1.5 mL microfuge tubes or 500 µL PCR tubes, which were suspended in a sonication bath above a 400 W (maximum power) Branson Sonifier ultrasonic horn. The samples were sonicated either with or without the presence of cleaned silicon dioxide or titanium dioxide beads for the desired amount of time at powers ranging from approximately 20 W to 80 W.

Along with each set of samples, positive controls (unsonicated bacteria at approximately 1000 colonies per plate) and negative controls (sterile broth used for dilution) were cultured alongside to the experiment. The effectiveness of the experiment was determined by counting colonies on the plates after incubation. Sample size in most cases was 1 mL.

The results of an *E. coli* lysing experiment were as follows. Sonication took place at approximately 70 W for various times (30 s, 2 minutes and 5 minutes) with and without the addition of 50 mg of cleaned silicon dioxide beads. It was observed that, with the addition of beads, approximately 2 minutes of sonication was sufficient to lyse most of the cells. Sonication attempts with the addition of beads appeared to be slightly more effective than attempts without beads. In the case of *B. Globigii* spores, a full 10 minutes of sonication at approximately 70 W with or without beads was necessary in order to thoroughly lyse the samples.

In other experiments, it was found that partial lysing could be obtained in smaller amounts of time (e.g., 5 min and 7 min samples) at approximately 70 W, and that the ultrasonic power delivered to the sample seemed to be the most important variable. For low power experiments with power set below 40 W, even a 10 minute lysing cycle had little effect.

In one embodiment, ultrasonic power is delivered through a computer-controlled power supply that allows the user to specify the power level, frequency, and waveform remotely. Sonication may be pulsed or continuous and may be as brief as a single 1 second pulse. Sonic horns are connected to this supply and machined to the correct width. Suitable frequencies include, but are not limited to, 29 kHz, 40 kHz, and 1 MHz. A flow chamber was milled with appropriately sized sample cells and mounted on the top of the horn. Using a miniature pump, samples were lysed in a completely automated fashion. Although the current prototype accommodates only four samples simultaneously, extending the number of samples processed simultaneously is straightforward.

Nucleic Acid Extraction Module

Once nucleic acids have been released from the sample, a purification and buffer exchange takes place. This step is to remove PCR-inhibitors and cell debris that could clog the device, and to exchange the sample fluid for a buffer that is PCR compatible. To achieve automation, laboratory methods involving precipitation and centrifugation are replaced with solid phase extraction methods.

A number of different materials were tested for their ability to bind and then release nucleic acids, including associated secondary-fibril cellulose, titanium dioxide beads and substrates, silicon dioxide beads and filters, chemically modified silica beads and filters, glass, commercial kits such as those sold by Qiagen and Invitrogen, and electric fields. The two technologies with the best yield were microliter-sized chromatography columns filled with RCA-cleaned silicon dioxide beads and separation chambers filled with beads from Invitrogen's charge switch nucleic acid extraction kit.

Human genomic DNA was prepared for the experiments by fragmenting with the McrBC restriction enzyme. This was used because it was found that, for all methods tested, efficiency of hybridization was lower when binding extremely large oligonucleotides. Once cleaved, the DNA was diluted in TE buffer to the desired concentrations at pH 7.

Spherical silicon dioxide beads in the size range of 40-75 µm were cleaned according to the RCA protocol, which includes exposures to hydrochloric acid-methanol, sulfuric acid, and boiling water, before drying in an oven. Various sized chromatography columns (2 µL, 4 µL, and 6 µL) were fabricated in solid blocks of PMMA with a Haas mini-Mill. The columns used standard chromatography fittings as fluidic connections, and titanium HPLC frits with 2 µm porosity were used to retain the packing material. The beads were packed into the columns using a syringe and 10 mM Tris-EDTA buffer (TE) at pH 8.4.

In preliminary experiments with silicon dioxide, a 200 µL sample containing fragmented human genomic DNA was first mixed with 200 µL of 50% isopropanol-50% 6 M guanidine hydrochloride solution for binding. This solution serves both to create binding affinity as well as to inhibit any nucleases in solution. The 400 µL mixture was then passed slowly over the column, either under pressure or under vacuum. The column was then rinsed with 250 µL of either ethanol or a 50% ethanol-50% DI water mixture, dried with air, and eluted with a 50 µL aliquot of 10 mM TE buffer, which is compatible with PCR procedures.

In preliminary experiments with Invitrogen charge switch beads, the manufacturer's protocol was modified to make it amenable to automation. 10 µL of charge switch beads were added to 200 µL of purification buffer (potassium acetate with potassium chloride), and then 200 µL of sample was added. The beads were agitated by gentle sonication for 15 s and then allowed to sit for 1 minute. A magnet was placed against the side of the reaction chamber so that the liquid could be pumped out without losing the beads. Next, 250 µL of wash buffer was pumped in and the beads were dispersed by a gentle, 15 s sonication. The wash buffer was allowed to sit for 1 minute and then removed. Finally, 50 µL of 10 mM TE buffer was added to the chamber, mixed by gentle sonication for 15 s, and collected for analysis.

Figure 3A:
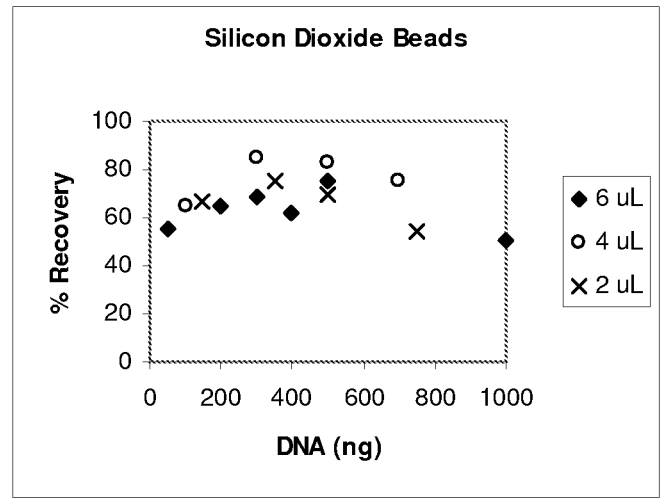
FIG. 3 shows plots of recovered DNA following lysis by sonication.
Figure 3B:
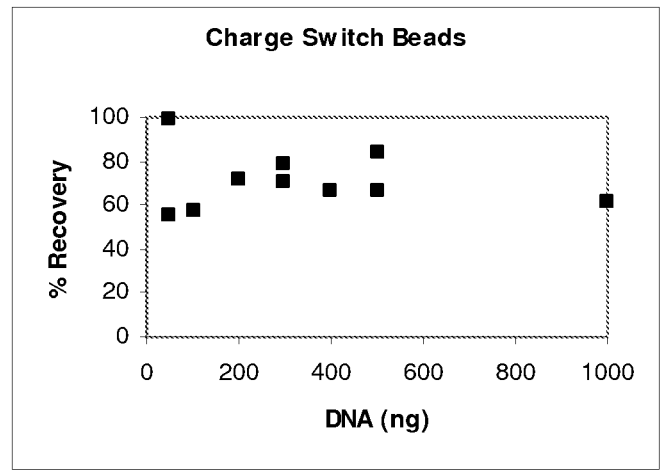

After the experiment, samples were diluted and then analyzed for residual DNA with the picoGreen stain from Molecular Probes. FIG. 3(*a*) shows typical results for RCA-cleaned silicon dioxide beads. It can be seen that 60-90% recoveries could be routinely achieved for a variety of different column sizes. In FIG. 3(*b*), typical recoveries are presented for Invitrogen's charge switch beads. In this case, 70-90% recoveries were typical. The primary difference between the two techniques is that the charge switch extraction can take place in less than 5 minutes. However, the silicon dioxide beads require approximately 20 minutes or more to obtain a good yield.

The lysing and extraction may be directly integrated. The procedure would be to sonicate in the presence of the RCA-cleaned silicon dioxide beads, and then extract nucleic acids from the beads using a titanium frit to retain the beads. An initial experiment indicated that this method reduces the complexity of the microfluidics compared to using two separate components. Preliminary data suggests that charge switch beads are effective at extracting RNA.

Selective Solid Phase Subtraction/Enrichment Process

The selective capture of specific oligonucleotides from complex matrices may enhance the detection sensitivity by removing genomic background from the samples prior to amplification. This process can be performed by covalently immobilizing capture probes that will hybridize with its complementary targets. Since this capture is commonly done by forming double strands of target sequences and capture probes, the double strand oligonucleotides may be denatured at high temperature to allow the binding of target strands to the capture probes in the presence of a high salt buffer. Also, the hybridization kinetics of oligonucleotides on a solid phase differ significantly from those in solution due to steric constraints of the immobilized capture probe and electrostatic charges at the surface. A properly functioning a selective solid phase (SSP), which may be in the purification chamber or in one more reservoirs coupled to the purification chamber, may have the following three characteristics: chemical stability at high temperature (~95° C.) in high salt environments (~3 M NaCl) to avoid shedding of the capture probes from the surface during the denaturation step; enough spacing between the surface of the solid support and the capture probe to reduce the steric constraints during the capture of the target; and charge neutrality to maintain the stability of the probe-target duplex after the capture.

A selective solid phase (SSP) with dendrimer-based chemistry capable of subtracting human genomic DNA from a complex mixture containing pathogenic DNA and RNA may be used. The branched structure of the dendrimer provides spacing between the surface and the capture probe and its charge neutrality avoids the interference of surface charges in the stability of the probe-target duplex. After the dendrimers have been covalently linked to the surface, then specific aminated capture probes can be covalently attached to the dendrimers' branches.

For the SSP-based subtraction, nasal washes containing NA from adenovirus and influenza A virus were used as a model to demonstrate the function of SSP. After an initial Reverse Transcription (RT) step converting influenza A virus (Flu A) RNA to its complementary DNAs (cDNAs), the samples were subject to a restriction enzyme digestion step to cleave the human genomic DNA in smaller fragments that are more efficiently captured by the solid phase. The sample was then exposed to the solid phase and heated up to 95° C. in the presence of a buffer containing SDS and NaCl. The human genomic DNA was captured and removed by the capture probes immobilized on solid phase. The recovered supernatant showed a reduction of the human genomic DNA by 80%. Further characterization of the pathogen NA after subtraction using polymerase chain reaction (PCR) in conjunction with Affymetrix re-sequencing microarray showed minimal lost of pathogen NA during the process.

The SSP can also be used as an enrichment process to capture the pathogenic targets and recover them for further amplification and detection. This concept utilizing nasal washes containing Flu A RNA has been demonstrated. In this case, the cDNA from the Flu A was retained onto the solid phase by specific capture probes using the similar process as above. The background matrix, such as genomic DNA from human cells and commensal organism, was removed. Then the Flu A DNA was recovered form the capture probes for downstream processing. The result showed that the enrichment process greatly reduced the background DNA and possible PCR inhibitors, to thus increase the detection limit of the downstream amplification process. Pathogen DNA recovery ranged from 70-80% by quantitative PCR.

Reverse Transcriptase and PCR Module

The system can include on-chip heated channels to perform the reverse transcriptase and polymerase amplification reactions. On-chip PCR devices have been described in the literature and documented to significantly reduce the amplification time due to the capability for rapid thermal cycling. Integration of the thermally controlled channels into the automated system may not only speed up the process and simplify operation by eliminating manual materials transfer, but may reduce the chances for contamination of subsequent samples by PCR amplicons through the use of fully enclosed on-a-chip components.

The automated system can integrate the 10-channel PCR component from Microfluidics Systems, Inc. as an example. The current design may be extended or replicated to include the reverse transcriptase reaction on the front end. Alternatively, isothermal polymerases can be used without a heater element, although the time required for amplification may be extended.

Fragmentation and Labeling Module

The fragmentation and end-labeling steps can be automated using a prehybridization component in the final device. The procedure includes a restriction enzyme digestion to break the nucleic acids into fragments of 25-100 base pairs, and an end labeling reaction with biotin that results in the controlled attachment of fluorophores to the captured target after hybridization. Options for fabrication include: (1) the development of a temperature controlled chamber downstream from the PCR channel preloaded with enzyme and biotin and (2) the incorporation of the fragmentation/labeling reaction at the downstream end of the PCR channel with addition of in-channel mixers, enzyme reservoirs, and enzyme addition ports. The system may include a restriction enzyme reservoir coupled to the fragmentation chamber, a lyophilized restriction enzyme may be in the fragmentation chamber and/or a biotin reservoir coupled to the fragmentation chamber.

Washing, Staining and Hybridization Module

Affymetrix gene chips have powerful resequencing capabilities because of the near-zero false positive capability, strain-level information, and the potential to identify emerging species. However, the internal volume of the Affymetrix chips is large (200 µL), and there are no mixing devices built into the inside of the chip case. Furthermore, due to the way in which the housing is constructed, it is not possible to remove the chip from the case for hybridization/staining and then replace it again for scanning purposes.

A mixing method for use with Affymetrix resequencing chips that reduces diffusion limitations and shortens the hybridization, without modifying or moving the housing of the gene chip has been developed. The current mixing method of rotating the housing with an air bubble inside to mix the sample fluid is not amenable to automation in a small system. As an alternative, a secondary chip housing was designed that could be connected to a peristaltic pump. The secondary chip was milled out of a Plexiglas block and had sealed inlets and outlets into the chip for fluid circulation. Silicone rubber tubing was attached to the ends and wound through a peristaltic pump with home-built custom software controls. The entire device was placed into an oven in order to maintain the 45° C. required temperature. Heating foil was also placed next to the chip instead of using an oven. One or more wash or stain reservoirs may be coupled to the microarray chamber.

Hybridization experiments were run using the custom setup described above and compared to static binding samples. Washing and staining was accomplished with the Affymetrix fluidics workstation, and the chips were scanned with an Affymetrix confocal scanner. Commercial software was used to make the base calls.

Figure 4A:
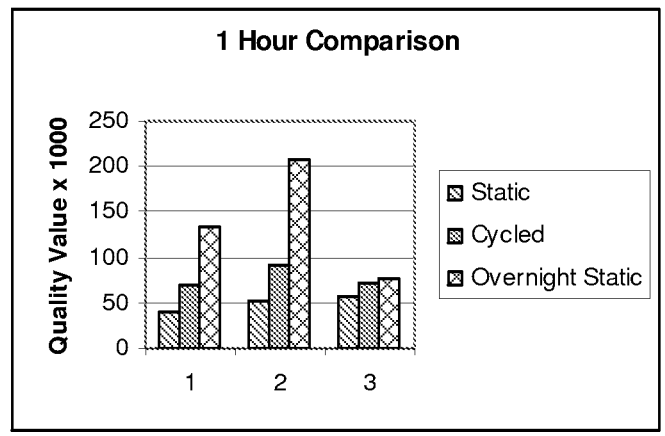
FIG. 4 shows plots comparing hybridization results using different methods.
Figure 4B:
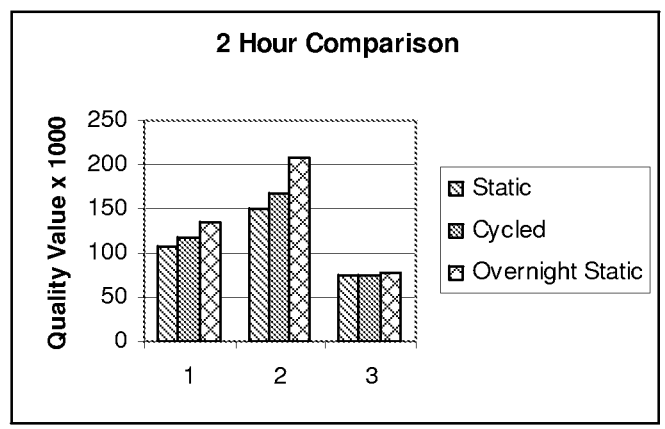
Figure 4C:
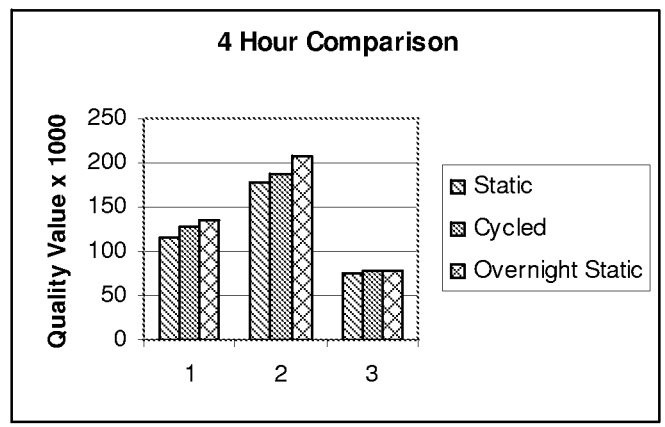

Results for 1, 2, and 4 hour hybridizations are presented in FIGS. 4(*a-c*). Data is for short time, recirculating pumping experiments from the new setup, short time static experiments, and overnight experiments (about 16 hours). From the data, it can be seen that a 1 hour re-circulating hybridization is not sufficient to capture a large amount of the target DNA in solution. By contrast, both 2 and 4 hour runs are able to hybridize with only a 10% loss on binding compared to overnight hybridizations. The data shows that it is possible to improve the hybridization time on Affymetrix resequencing chips by introducing a re-circulating flow through the chamber with a peristaltic pump.

The housing limitations of Affymetrix chips can be overcome for reasonable hybridization times. There is a dependence between the required hybridization time and the concentration of solution introduced into the chip, although the results indicate that in cases where it is important, recirculation can be used to improve hybridization times.

A preliminary device component has been fabricated capable of performing all of the pre-hybridization, hybridization, washing, and staining steps that are currently performed by a combination of manual steps and several large pieces of Affymetrix equipment. This new device is small and completely automated, and takes advantage of the hybridization speed-up results to minimize time requirements. The inputs for the device component are the fragmented sample and reagents. After running the device, the result is a completely hybridized and stained chip that is ready to be scanned. Rather than using an oven to control the temperature of the chip, resistive heaters made from thin foil are used to reproducibly heat the chip. These heaters contain feedback loops to minimize temperature fluctuations, and are interfaced with a computer for complete automation using in-house designed software. The entire component, including pumps, valves, gene-chip housing, and electronics has a footprint about the size of a textbook when properly assembled. Most of the parts can be replaced with disposable ones.

Systems Integration

In an integrated system, initial testing focuses on the compatibility of different components with each other by running operations in series with manual intermediate steps. Once module compatibility has been established, automation issues are addressed with the final result being a system where all individual units are attached to each other. Passive mixers are added to and between components where required. Microfluidic valves and pumps are selected and optimized for reproducibility and reliability in order to assemble the system. In addition, a software interface is developed to link the operation of the individual modules. Strict timing can be implemented within and between units, and checks and balances can be introduced to make sure that samples are not destroyed or lost during the automated protocol.

Advantages of the system may include one or more of the following. It can be easy to use without a highly skilled operator with molecular biology expertise. It may eliminate potential for cross contamination during processing, as each sample is totally enclosed in independent fluidic path until the microarray is completed. It may reduce operating time by eliminating manual fluid transfers, implementing rapid heating/cooling cycles at multiple steps, and expediting microarray hybridization and staining. It may be safer for processing of infectious samples since all steps are enclosed. It may provide for parallel processing of multiple samples. It may be smaller with reduced power requirement compared to current systems using robots or manual procedures with standard thermocyclers. It may be adapted for use with or without random amplification. It may be adapted for use with spotted or photolithographic microarrays.

The system is described in terms of components that make up the complete automated system in order to process a sample for a variety of applications and perform gene-based analysis. The components can be varied to accommodate a variety of analytical requirements. Some of the options may include:

Sample type: Samples may be aqueous solutions or suspensions when introduced into the system. The samples could be of environmental, clinical, veterinary, agricultural or food origin.

Cell lysis: The lysis must be sufficient to release encapsulated oligonucleotides. If the target is RNA, the conditions must preserve its integrity. However, methods of use could include but are not limited to sonication, mechanical motion, electrolysis, chemical disruption/dissolution, enzymatic degradation (such as proteinase K or lysozyme) and/or heat.

Nucleic acid purification: The target oligonucleotides may be separated from sample components that interfere with reverse transcriptase or polymerase in a method amenable to automation. For this reason, solid phase separation may be used to adsorb the targets. Materials could include but are not limited to silica (glass), titanium dioxide, silicon, cellulose, or charge-switch beads.

Separation of target and sample oligonucleotides: The separation of target and sample oligonucleotides is generally not required if specific primers are used for amplification. However, if random or degenerate primers are employed, host oligonucleotides may also be amplified, reducing the sensitivity of the assay for the target. A solid phase separation component may be added to the system to either bind the sample oligonucleotides and pass the target oligonucleotides in a subtraction mode or to bind the target oligonucleotides for elution subsequent to removal of unbound oligonucleotides from the sample matrix in an enrichment mode. This step can be very useful if the microarray is to be used to determine sequence information on rapidly evolving organisms or on targets where strain information is important for therapy, epidemiology, or forensic attribution.

Fragmentation, labeling, and staining components: The exact chemistries, temperatures, times, and volumes for these operations can be varied to accommodate the type of microarray and readout mechanism. A wide variety of protocols are described in the literature. In general, the higher the resolution of the microarray, the more demanding the staining protocol in terms of number of steps and precision of fluid delivery.

Hybridization: The amplicons of the target oligonucleotides must have sufficient time and exposure to the DNA microarray to bind to the capture probes on the array. In general, the longer the probes (e.g. ~75-mers in spotted microarrays compared to ~35-mers in photolithographically produced microarrays), the faster the binding. The component can use methods such as hydrodynamic flow, sonication, or electrophoretic forces to expedite delivery of the target amplicons to the microarray surface or simply take a longer time and let diffusion occur.

Fluidics: A number of different valve and pump technologies may be used, including but not limited to pneumatic valves, miniaturized solenoid valves, syringe pumps, roller pumps, and miniaturized peristaltic pumps.

Number of chips produced: The components can be made to handle one or many samples in parallel.

Having described the invention, the following examples are given to illustrate specific applications of the invention. These specific examples are not intended to limit the scope of the invention described in this application.

Example 1

Hybridization, Staining, and Washing

A "hyb-wash-stain component", has been demonstrated to expedite the processing of commercial microarrays. Affymetrix resequencing GeneChips designed for the detection of upper respiratory pathogens were used. The normal procedure for processing these chips is as follows: (1) Inject a sample containing biotinylated DNA and incubate in an Affymetrix rotisserie oven for 2-16 hours. Mixing is accomplished as an air bubble tumbles across the surface of the microarray. (2) Remove the hybridization mixture. (3) Stain and wash using a 3-step staining procedure in an Affymetrix wash station for 1.5 hours. (4) Image on a confocal scanner. While these protocols are acceptable for large centralized laboratories with trained technicians, they may not be optimal for portable devices for point-of-care diagnostics. If commercially produced nucleic acid microarrays are to be used in portable biosensors, it may be useful to design miniaturized and integrated devices that can perform all of the hybridization, staining, and washing steps necessary in an automated fashion. The hyb-wash-stain component described here is capable of performing these operations on Affymetrix resequencing GeneChips without evaporative losses and within a reasonable timeframe for a point-of-care biosensor. The device is small, completely automated, and has been designed for modular integration into a portable system that includes sample processing and nucleic acid amplification. Eppendorf tubes containing sample and reagents are inserted into holders on the device, and the result after processing is a hybridized and labeled microarray, ready for scanning. Results show that hybridization intensities and base calls are comparable to those obtained on the commercial system.

Tris, Tween-20, and normal goat IgG were purchased from Sigma (St. Louis, Mo.). SSPE was purchased from Ambion (Austin, Tex.). Phycoerythrin was supplied by Molecular Probes (Carlsbad, Calif.). Herring sperm DNA was obtained from Promega (Madison, Wis.). All other reagents were purchased from Affymetrix (Santa Clara, Calif.). Pre-hybridization buffer was a 10 mM TRIS buffer at pH 7.8, with 0.01% Tween 20. The hybridization buffer was a 10 mM TRIS buffer, with added control oligos, herring sperm DNA, and surfactants. Wash A solution contained 6×SSPE (saline/sodium phosphate/EDTA) and 0.01% Tween-20. Wash B solution contained 0.6×SSPE and 0.01% Tween-20. Stain 1 contained phycoerythrin dye, while stain 2 contained a biotinylated antibody. All solutions were made up in nuclease free water. Purified DNA from a field strain of adenovirus types 4 and 5 was kindly provided by Dr. Kevin L. Russell at the Naval Health Research Center (San Diego, Calif.). Microarray composition and hybridization details are described in a previous publication (Lin et al., *Genome Res.* 16, 527-535 (2006)).

The microarrays used in this study were Affymetrix resequencing GeneChips, custom designed for 20 common upper respiratory pathogens and 6 CDC category A bio-threat agents. In a typical hybridization experiment run on the hyb-wash-stain component, the chip was activated by circulating a pre-hybridization solution for 10 minutes at 45° C. The pre-hybridization buffer was then removed and discarded. Next, a sample containing adenovirus type 4 and 5 was introduced to fill the resequencing GeneChip and tubing, and was allowed to hybridize to the microarray under re-circulating flow in the automated device for two hours at 45° C. A sample concentration of 125 pg/mL was chosen because it can be realistically obtained from PCR amplification. Finally, a series of wash and staining steps using two separate washes and stains was performed in the following order: wash A, stain 1, wash A, wash B, stain 2, stain 1, wash A. In the hyb-wash-stain component, each washing step used 2 mL of buffer and lasted for 2 minutes. In each staining step, the resequencing GeneChip and tubing were filled with the stain and re-circulating flow was introduced for 15 minutes. All washing and staining steps took place at room temperature, with the exception of wash B, which took place at 45° C.

In order to evaluate the efficiency of the hyb-wash-stain component, hybridizations were also performed using commercially available Affymetrix equipment. GeneChips were pre-hybridized for 10 minutes, and then sufficient sample was introduced into the chip to leave an air bubble approximately 50 µL in size. Hybridizations were performed in an Affymetrix GeneChip Hybridization Oven, Model 640 for 2 hours at 45° C. The overall sample volume required for hybridization in commercial equipment was about half that required for the hyb-wash-stain component, since the commercial hybridization equipment had no associated tubing that needed to be filled. In this work, the DNA concentration was constant between the two devices (at 125 pg/mL), although it was observed in other experiments that small concentration differences such as a factor of 2 had very little effect on the hybridization efficiency (data not shown). In cases where staining and washing on commercially available equipment was also desired, an Affymetrix GeneChip Fluidics Station Model 450 was used. The sequence times and volumes of reagents used by the different pieces of equipment are shown in Table 1. Regardless of the hybridization or washing equipment used, all chips were scanned on an Affymetrix GeneChip Scanner 3000.

TABLE 1

A comparison of the solution volumes and circulation times used by the commercially available equipment and the hyb-wash-stain component. There were a total of four washing steps and three staining steps in the protocol. Times were not necessarily optimized.

|  | Commercial Equipment | Hyb-wash-stain component |
|---|---|---|
| Sample Volume | About 250 µL | About 400 µL |
| Wash Volume | About 8 mL | 2 mL |
| Stain 1 Volume | 600 µL | 600 µL |
| Stain 2 Volume | 600 µL | 600 µL |
| Hybridization Time | 2 hours | 2 hours |
| Wash Time | 7 minutes (×4) | 2 minutes (×4) |
| Stain Time | 10 minutes (×3) | 15 minutes (×3) |

The hyb-wash-stain component consisted of a single Instech peristaltic pump (Plymouth Meeting, Pa.), two commercially available Minco foil heaters (Minneapolis, Minn.), two Lee Company miniature 3-way valves (Westbrook, Conn.), and a 6-way Hamilton chromatography valve (Reno, Nev.). All components were interfaced to a computer via RS-232 communications using an Ontrak Control Systems A/D board (Sudbury, Ontario, Canada). Power was provided by a power supply from Sunpower Technologies, USA (Union City, Calif.), and a custom electronics control board. Control software written in ANSI C using Lab Windows from National Instruments Company (Austin, Tex.) provided automatic timing and control of all the components, allowing operation without user intervention.

The device that held the Affymetrix GeneChip itself, as well as the pump, the two Lee valves, and the two heaters, was contained inside an insulating Plexiglas box. The dimensions of the insulated box were 2.5"×3"×3.5". The chip was inserted into a window in the front of the box and secured using a pair of screws.

Obtaining adequate mixing within the Affymetrix GeneChip itself is necessary in order to minimize hybridization times, as well as to obtain uniform hybridization efficiency across the surface of the microarray. Affymetrix suggests an overnight hybridization (16-24 hours) in a rotisserie oven, where even mixing is facilitated through the motion of an internal bubble. It was found that the hybridization time can be reduced to four hours with good results, and in some cases, can be made as short as two hours (data not shown). However, the rotating mixer provided by Affymetrix would be difficult to miniaturize due to the large number of moving parts that would be required.

As an alternative to a rotisserie hybridization oven, the hyb-wash-stain component uses a continuously re-circulating fluid flow through the GeneChip to facilitate hybridization. Although hybridizations performed under fluid flow have been shown to be effective for spotted arrays (Benn et al., *Anal. Biochem.* 348, 284-293 (2006)), this study is more limited due to the fact that the internal chamber of the GeneChip cannot be modified. The large internal volume of the chip (approximately 300 µL) is particularly disadvantageous, because the sample must be sufficiently diluted to fill both the chamber and any accompanying tubing, which compromises hybridization time. In addition, the internal geometry is fixed, so that the shape of the flow profile cannot be adjusted.

It is important to ensure that the sample is well mixed and flows continuously over the entire microarray surface, because the probes for different pathogens are located on different areas of the microarray. In a well-designed flow hybridization chamber, convective transport of the nucleic acids to the target sites will result in a fast hybridization. For this reason, it is important to verify that there are no stagnant regions in the flow profile under realistic experimental conditions. Stagnant regions would rely on diffusive transport of the nucleic acids to the probe sites, resulting in a very slow hybridization. A 20 µL plug of food dye was injected into the flow over the GeneChip and imaged using a cooled CCD camera. Using fluorescence imaging, the steady-state flow profile of the sample through a GeneChip was visualized. Observations show that flow rates are largest along the middle of the chip in a path connecting the inlet (bottom center) and outlet (top center) of the chip. However, the flow moved radially outwards from the entrance of the GeneChip, and eventually reached all areas in the microarray. With this type of flow profile, it is expected that hybridization times will be slower near the corners of the microarray and faster near the center. Experiments demonstrate that despite this flow profile, sufficient exposure and mixing took place to produce hybridization results comparable to those obtained using the commercially-available rotisserie mixer.

In order to demonstrate that the hyb-wash-stain component can duplicate the results of the commercially-available Affymetrix equipment, a series of experiments was set up as follows. Each experiment involved hybridizing targets from Adenovirus types 4 and 5 to three separate microarrays. In run A, all operations were performed using the hyb-wash-stain component. In run B, hybridization took place on the commercial equipment, but staining and washing took place in the hyb-wash-stain component. In run C, the entire hybridization, staining, and wash procedure was run on commercial equipment. This experiment was performed in triplicate. A blank run was also performed where the chip was hybridized on the commercially available equipment, but with the sample replaced by hybridization buffer. All hybridizations took place over a 2 hour period.

Images of scanned chips showed that comparable regions of the chips were hybridized by all of the methods described above. The average base call percentages for each run are presented in Table 2. There were three sets of gene sequence regions or tiles for Adenovirus type 4, and two for Adenovirus type 5. In all cases, the percentage of bases called were comparable for the three hybridization methods, proving that the hybridization and staining device is as effective as commercially-available equipment.

TABLE 2

| | Average base call percentages for Adenovirus type 4 and Adenovirus type 5 tiles. | |
|---|---|---|
| Run | Adenovirus type 4 (Tile 1/Tile 2/Tile 3) | Adenovirus type 5 (Tile 1/Tile 2) |
| A | 37%/86%/62% | 73%/91% |
| B | 36%/88%/63% | 82%/91% |
| C | 37%/87%/64% | 82%/94% |

In addition to achieving comparable results, the hyb-wash-stain component had a number of potential advantages over commercial equipment. First, the device is completely integrated, so that the nucleic acid microarray never has to be manually moved between pieces of equipment during the protocol. This helps prevent inadvertent contamination as well as operator mistakes, and makes the use of our device less labor intensive. Furthermore, the size of the hyb-wash-stain component is significantly smaller than that of the commercial equipment, which has the footprint of a typical laboratory benchtop. Finally, the device uses smaller amounts of the washing buffers, and washing times are shorter. No evaporative or other losses of solution were observed in the system during hybridization runs.

Example 2

Lysis and Purification of Nucleic Acids

Reagents and materials: Binding buffer PB was obtained from Qiagen. PBS was made by mixing a powder packet from Sigma into 1 liter of nuclease-free water. MasterPure DNA purification kits came from Epicentre and were used according to the manufacture's recommended protocols. SDS solutions were made from a 10% SDS stock from Ambion. Human genomic DNA (Roche) used for testing bead extraction was first subjected to a restriction enzyme digestion (MCrBC enzyme, reagents, and protocol from a New England Biolabs kit). Three types of beads were tested: silicon dioxide powder with a size range from 200 nm to 10 µm (approximately 80% between 1-5 µm) obtained from Sigma, spherical silica gel with a size range of 40-75 µm obtained from Silicycle, and glass beads with a size range of 30-50 µm obtained from Polysciences. Nasal wash in sterile PBS was obtained from human volunteers and was not screened for other pathogens. The Sybr-green kit (Molecular Probes, Invitrogen) used for real-time PCR was obtained from Qiagen.

Standards: Every set of lysis experiments contained control samples in which cells in spiked buffer were subjected to the MasterPure purification protocol. The MasterPure extraction was considered the "gold standard" and the amount of DNA recovered from the control samples was set as 100%; lysis efficiencies for the remaining experimental samples were calculated relative to the MasterPure control samples for each experiment.

Lysis: Lysis efficiencies were tested with *E. coli* and Cyd-x, the commercial name of *Cydia pomonella* granulovirus. *E. coli* was obtained from overnight cultures grown in LB broth with shaking at 37° C. and stored at 4° C. until use. Cyd-x was a sample provided by Certis USA. To better approximate clinical or field conditions, both model pathogens were used exactly as obtained; after mixing of the storage tube, bacteria or virus in broth/transport medium was spiked directly into buffer (TE or PBS) or nasal wash without washing or resuspension. The spiked sample, usually 150 μL, was mixed with an equal volume of lysis buffer in a 1.7 mL Eppendorf tube and allowed to incubate on the benchtop. For sonicated samples, the tip of a Branson Sonifier 450 probe was inserted into the liquid and the tube was clamped into place. Sonication times varied from 1 second to 5 minutes, with duty cycle at 50% and power from 50-85 W. The tube was immersed in an ice bath for longer sonication times to help prevent frothing.

Lysis measurement: Initially, after treatment 10 μL of each sample was plated onto agar plates and cultured in a 37° C. incubator overnight. Lysis efficiency was calculated by counting colonies and comparing to a control plate containing 10 μL of untreated cells spiked in buffer. Later, for faster and more quantitative assessment of the amount of amplifiable nucleic acid released, lysed samples were precipitated using the post-lysis portion of the MasterPure purification protocol and real-time PCR. A standard curve was constructed from a dilution series of pathogen DNA over six orders of magnitude. These six samples were included in the real-time PCR and used to relate each sample's threshold cycle number to the initial concentration of DNA in the sample. Each sample was amplified in replicate reactions, and the calculated copy numbers were averaged. DNA recoveries were also visualized by gel electrophoresis on 1.2% TAE agorse gel, post-stained with Sybr Gold (Molecular Probes, Invitrogen).

Sonication was chosen for its potential for miniaturization and previously demonstrated quick and complete cell disruption. It also proved to be effective at homogenizing the samples and reducing clumping in viscous samples such as nasal wash. Initial experiments involved direct sonication of *E. coli* spiked into TE buffer and plated on LB plates. Plate counts showed a significant reduction in colony forming units after just 30 seconds of sonication. However, since culture methods did not provide information on the amount of usable DNA released by the cells, real-time PCR was chosen as a more informative quantification method.

Chemical lysis in conjunction with sonication was also an attractive option for automatable nucleic acid purification because of its simplicity. Additionally, chaotropic salt solutions have three favorable properties for sample preparation—they lyse cells at high concentrations, they denature nucleases to protect the released nucleic acids, and they promote the binding of nucleic acids to silica substrates. The ability of the chaotropic salts to protect nucleic acids was a critical feature when dealing with complex clinical samples such as nasal wash. The Qiagen binding buffer (which contains guanidine hydrochloride in isopropanol (U.S. Pat. No. 6,383,393)) was chosen for its convenience and safety compared to guanidine isothiocyanate, which releases cyanide gas under acidic conditions. In all cases, the volume of lysis buffer added was equal to the sample volume, so that concentrations of lysing reagents would not vary from experiment to experiment.

Figure 7A:
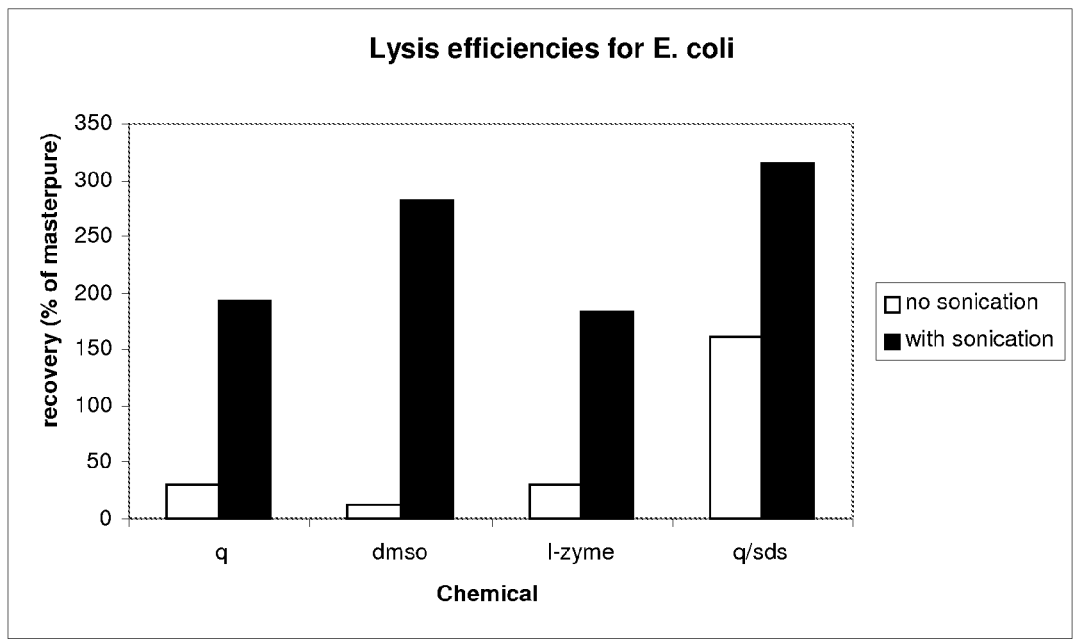
FIG. 7 is a plot of (a) *E. coli* and (b) Cyd-x lysis efficiencies (as a percent of the amount of DNA recovered from identical samples using the MasterPure kit) for various chemical lysis buffers, with and without sonication. The column labeled q represents samples exposed to Qiagen buffer. The column labeled DMSO denotes samples exposed to 10% DMSO in Qiagen buffer. The l-zyme column is for samples exposed to a 1 mg/mL lysozyme solution for 30 minutes, followed by the addition of Qiagen buffer. The q/sds column is for samples exposed to Qiagen buffer with 0.1 wt % SDS added.
Figure 7B:
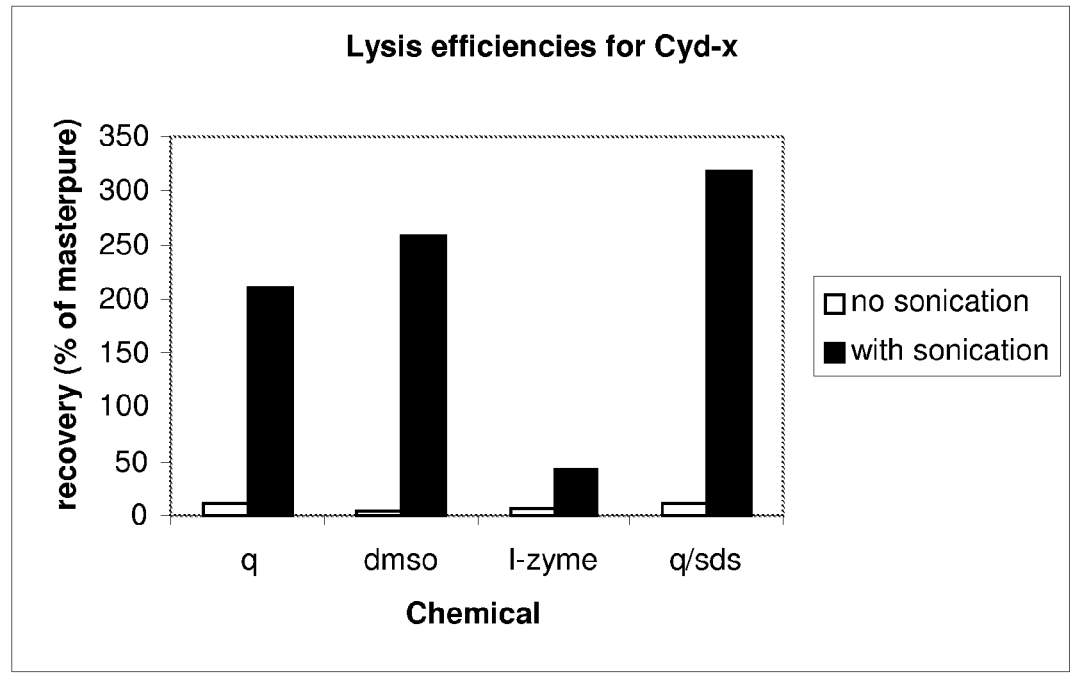

Several mixtures with the Qiagen buffer were tested, including 10% DMSO, and 0.1 wt % SDS. In addition, 30 minute pre-treatment in 1 mg/mL lysozyme was investigated. The purpose of the additives was to help solubilize the cell membranes to aid in splitting open the cells and releasing nucleic acids into solution. SDS proved to be the most effective, with higher recoveries than Qiagen buffer alone or other mixtures (FIG. 7). The addition of a sonication step was more effective than any combination of pure chemical lysis methods alone. Trends were similar across both *E. coli* and Cyd-x, as shown in FIG. 7.

Lysis by purely chemical means required an incubation period, and was not very effective for Cyd-x. With the addition of SDS to the lysis buffer, *E. coli* lysis comparable to that from MasterPure could be achieved in 30 minutes, but an hour of incubation with Qiagen buffer/SDS only resulted in 15% of the MasterPure recovery for Cyd-x. Combining the chemical and physical lysis resulted in full disruption of both *E. coli* and Cyd-x, and the release of nucleic acids with minimal incubation. The power applied during sonication and the duration of sonication were both important factors in the effectiveness of lysis and the recovery of intact, amplifiable nucleic acids. Insufficient time or power resulted in a smaller amount of released nucleic acids, but overexposure resulted in degradation of the DNA and reduced PCR amplification.

Bead extraction: Extraction was tested using purified human genomic DNA (Roche Applied Science) that had been fragmented by McrBC (New England Biolabs). The glass beads were cleaned by soaking in a mixture of 50% hydrochloric acid, 50% methanol for one hour, followed by a one hour soak in concentrated sulfuric acid. The cleaned beads were then rinsed until neutral pH was obtained, boiled in distilled water, rinsed again, and finally dried in an oven. The beads were stored dry. Silica powder and silica gel were size-fractionated by settling in water, then stored at pH 2. Immediately before use, beads were washed in 100% ethanol, then aliquoted into sample tubes by pipet and dried on a heat block. Binding buffer and sample buffer were then added, and DNA was spiked in. Binding took place at room temperature, with tubes held horizontally on a vortex genie shaking adapter. Following binding, the beads were allowed to settle and the binding buffer was removed from the tube, leaving the beads at the bottom. The beads were washed with 500 μL of 70% ethanol and dried again. 20 μL of elution buffer was then added to the beads. The tube was taped shut and placed in a closed box fixed to the rotor in an Affymetrix hybridization oven. The oven was set to 55° C. and the rotor moved at 20 rpm so that the tubes rattled around in the box and dispersed the beads and elution buffer. After elution, the elution buffer was removed from the tube and 10 μL of each sample was used in two replicate real-time PCR reactions. The concentration of DNA in the elution buffer was calculated from the PCR standard curve and the calculated total amount of DNA in the elution buffer was compared to the known amount of starting material that was put onto the beads. Binding and wash fractions were also collected and precipitated using the post-lysing portion of the MasterPure protocol, in order to analyze the percentage of DNA captured by the beads and the amount lost before elution. Precipitated samples were resuspended in the same volume of elution buffer used for regular elutions.

Extraction measurement: Human genomic DNA samples (unbound, washed, and eluted fractions) were stained with PicoGreen (Molecular Probes, Invitrogen) and measured using a fluorometer. Samples precipitated using the MasterPure MPC reagent (Epicentre) tended to show inflated measurements (often over 100% of the starting material), so binding fractions (leftover DNA in the binding buffer after binding) may be overstated.

Pure Qiagen buffer and Qiagen buffer with 0.05-0.5% SDS by weight were tested for their ability to bind DNA to beads. Higher concentrations of SDS were more effective at lysing, but also were more likely to aggregate or precipitate, and inhibit downstream reactions. 0.05% SDS in Qiagen buffer was selected as having good lysing properties while also washing out of the sample and not interfering with PCR. Among the three types of beads tested, the glass beads showed the best and most consistent performance with SDS in the Qiagen buffer. Experiments showed that binding was strongly time and mixing dependent. The beads were relatively large (40-75 μm diameter) and settled quickly in the Eppendorf tubes. To increase contact between the beads and sample, a vortex shaker was used to keep the beads in suspension. Higher intensities of gentle vortexing and longer times both increased binding, shown by smaller amounts of DNA that could be recovered from the binding buffer removed from the beads, indicating that DNA had bound to the beads. After 5 minutes of shaking human genomic DNA sample with beads in Qiagen binding buffer, the glass beads had bound only 18% of the DNA. After 20 minutes 70% was bound. The silica beads performed half as well as the glass over shorter binding times. After 60 minutes all three bead types had bound 80-90% of the DNA, but this was considered too long.

The effects of temperature and buffer pH were also explored. Temperatures up to 45° C. did not affect binding, but eluting at 60° C. greatly decreased the required elution times. Higher temperatures decreased elution recoveries, possibly because the DNA was denatured. Increasing the elution pH from 8.6 to 9.2 also produced higher yields without inhibiting PCR. In general, a list of parameters studied and conclusions regarding sample preparation are listed in Table 3.

TABLE 3

Parameters tested and their effect on the lysing and extraction process

| Parameter | Impact | Optimized conditions |
|---|---|---|
| Lysis incubation time | Longer times lead to more complete lysing | Not necessary for *E. coli* with sonication. For spores, either a 15 min+ warm incubation before sonication or a longer/more intense sonication is needed. |
| Chaotropic salt concentration | Higher -> better binding | Qiagen buffer is supplied at approximately 5M guanidine HCl. Also tried pure guanidine hydrochloride diluted to various concentrations in buffer and it worked as well |
| SDS concentration | More SDS leads to better binding, but above 0.1% can precipitate out of solution near room temperature, resulting in poor mixing, and can potentially cause clogging in an automated device or inhibit PCR | 0.05% |
| Sonication | Longer times or higher power increases lysing but decreases DNA quality | 5 one-second pulses was sufficient for *E. coli* lysis |
| Binding time, agitation | More time is better up to ~1 hour, shaking or some other method is necessary to disperse beads. | +80% binding can be reached in 30 minutes with moderate shaking. |
| Binding temperature | No effect | Room temperature |
| Wash | Is needed to remove salts. Poor recovery was observed without wash | One wash with 70% EtOH, using ~2x the total binding volume. |
| Elution time/temp | Elevated temperature increased elution rate, but too high of a temp caused denaturation. DNA could bind to beads in TE at pH 8. | 60° C., pH 9.2 |

TABLE 3-continued

Parameters tested and their effect on the lysing and extraction process

| Parameter | Impact | Optimized conditions |
|---|---|---|
| Elution volume | Larger volume leads to faster elution, but lower concentration | 20 μL |
| Amount of beads | No difference was observed in binding capacity between 2 and 40 μL of beads | 5 μL for a 150 μL sample |

Sample preparation and detection: To demonstrate the entire protocol, *E. coli* were transformed with two plasmids containing markers for the HA and crmB genes from Variola major virus (vmv). Plasmid uptake was confirmed by extraction using a Miniprep cleanup kit (Qiagen) and visual verification on a gel. *E. coli* was spiked into PBS and nasal wash samples and processed according to the sonication and chemical lysis protocol, followed by extraction using glass beads as described above. Samples were each eluted in 20 μL of TE at pH 9.2. Half of each sample was used for real-time PCR, and the other half was then processed and hybridized to a resequencing array. Briefly, multiplex PCR was performed (the reverse transcription step was omitted since the amplification target was a DNA plasmid). The PCR product was then fragmented, labeled, and hybridized to a NRL RPM v1 Affymetrix resequencing chip for 4 hours. The chip was washed, stained, and scanned. Base call data was analyzed and pathogens identified using software developed at the Naval Research Laboratory.

*E. coli* containing two vmv plasmids was spiked into PBS and nasal wash, then processed according to the developed protocols. Recovery of nucleic acids from both PBS and nasal wash was confirmed by gel electrophoresis, amplification of *E. coli* chromosomal markers in real-time PCR, and amplification of the vmv sequences by multiplex PCR and detection on the NRL RPM v1 resequencing chip (Lin et al., *Genome Research,* 16, 527-535 (2006)). (Table 4). Nasal wash samples spiked with *E. coli* were also subjected to the lysing and extraction protocol we developed, and both vmv genes were identified on the resequencing chip. Reported base calls for these genes are shown in Table 4.

TABLE 4

Resequencing chip results for *E. coli* lysed and purified by various methods and spiked into both buffer and nasal wash. The base calls are sufficiently high to provide enough sequence information to identify the gene and the organism in all cases.

| Sample | Description | Base Calls (Tile A/Tile B) |
|---|---|---|
| 1 | MasterPure lysing and purification (control) in nasal wash | 57%/87% |
| 2 | *E. coli* in TE, extracted with glass beads | 85%/75% |
| 3, 4 | *E. coli* in nasal wash, extracted with glass beads | 75%/82%<br>82%/89% |

The entire protocol was designed to eliminate use of enzymes and organic solvents for easier storage, use, and disposal. All reagents can be kept at room temperature with no special precautions, and there are no precipitation, centrifugation, or cooling steps that would require the use of large equipment not suitable for field testing. The entire sample preparation protocol can be completed in less than 60 minutes, and the nucleic acids obtained were of sufficient quality for PCR amplification and detection on resequencing microarrays.

Example 3

Disposable Devices

Figure 5:
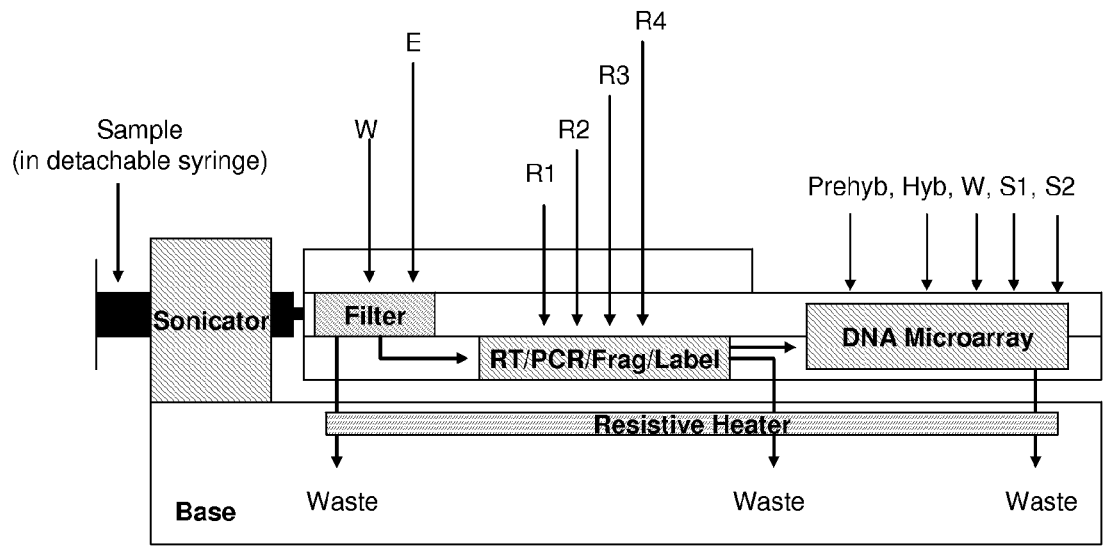
FIG. 5 schematically illustrates a disposable device using lysing in a detachable syringe.
Figure 6:
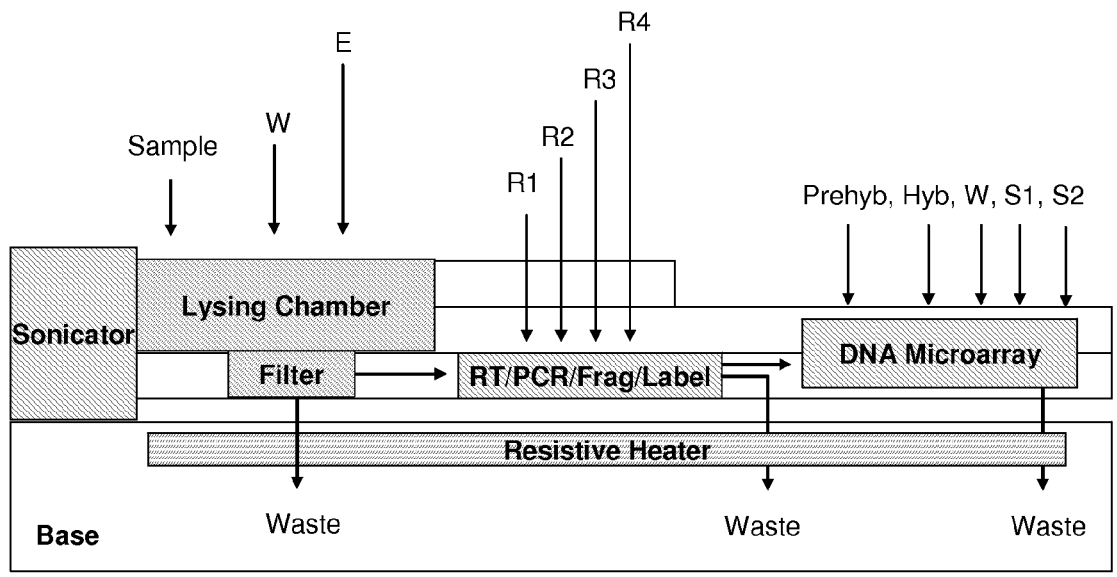
FIG. 6 schematically illustrates a disposable device using a lysing module.

FIGS. 5 and 6 schematically illustrate disposable components that are placed on a base device. The base contains the components for sonicating, pumping, and heating the sample in the various parts of the disposable device. The disposable device contains all the chambers, ports, and possibly reagent reservoirs or inputs. The fluidic paths are shown by arrows. The added reagents are labeled as follows. "Sample" is the sample input stream. "W" is a wash input line. "E" is the elution input line. "Waste" is one of the outlet lines from any module. "R1" is an input line for reverse transcriptase reagents. "R2" is an input line for PCR reagents and primers. "R3" is an input line for Fragmentation enzymes and buffers. "R4" is an input line for labeling reagents and buffers. "Prehyb" is an input line for the prehybridization buffer. "Hyb" is a cocktail containing the hybridization reagents. "W" is an input line for the wash buffer. "S1" is an input line for stain 1. "S2" is an input line for stain 2. There is a filter or frit attached to the lysing chamber, either for holding the solid phase extraction beads in the chamber, or as a solid phase extraction material itself. All input lines can also flow air, if needed. Other air inlet lines may be added. Vents, hydrophobic membrane materials, and/or bubble traps may be added to remove trapped air in the system. A single or multiple resistive heater(s) are mounted in the base to provide temperature control. The base contains multiple pumps, such as 2-3. Multiple valves are either integrated into the top, or contained in the base. An alternative design may include a second solid phase extraction step in between the RT/PCR and the fragmentation/labeling chambers.

In FIG. 5, lysing occurs in a detachable syringe, which can be provided pre-filled with reagents and possibly solid-phase extraction beads; or reagents can be added by the user at the time of use. Sonication takes place in contact with a horn (possibly hollow) or in a small bath.

In FIG. 6, lysing takes place in an attached chamber, pre-filled with reagents and possibly beads. Alternatively, lysing reagents and/or beads can be added along with sample. Sonication takes place in contact with a horn.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. An apparatus comprising:
    a housing;
    a sample port for placing a liquid biological sample into the housing;
    a microarray port for inserting a microarray having oligonucleotide probes thereon into the housing;
    a lysis module within the housing and coupled to the sample port;
    a purification module within the housing coupled to the lysis module and containing a solid phase comprising covalently immobilized capture probes that are capable of capturing 80% of human genomic DNA;
    a thermocycling module within the housing coupled to the purification module and capable of containing a polymerase chain reaction;
    a fragmentation module within the housing coupled to the thermocycling module; and
    a microarray module within the housing coupled to the fragmentation module and capable of holding the microarray and a liquid in contact with the microarray;
    wherein the apparatus is configured to be coupled to a device capable of:
        pumping a liquid through, in order, the lysis module, the purification module, the thermocycling module, the fragmentation module, and the microarray module;
        sonicating any contents of the lysis module;
        thermocycling the thermocycling module to perform the polymerase chain reaction;
        heating the fragmentation module to fragment any oligonucleotides contained therein;
        circulating a fluid over the surface of the microarray; and
        performing one or more washing or staining steps on the microarray.

2. The apparatus of claim 1, further comprising:
a lysis reagent reservoir coupled to the lysis module.

3. The apparatus of claim 1, wherein the thermocycling module is capable of containing a reverse transcriptase reaction.

4. The apparatus of claim 1, further comprising:
a restriction enzyme reservoir coupled to the fragmentation module.

5. The apparatus of claim 1, further comprising:
a biotin reservoir coupled to the fragmentation module.

6. The apparatus of claim 1, further comprising:
a lyophilized restriction enzyme within the fragmentation module.

7. The apparatus of claim 1, further comprising:
one or more wash or stain reservoirs coupled to the microarray module.

8. A method comprising:
providing an apparatus comprising:
    a housing;
    a sample port for placing a liquid biological sample into the housing;
    a microarray port for inserting a microarray having oligonucleotide probes thereon into the housing;
    a lysis module within the housing and coupled to the sample port;
    a purification module within the housing coupled to the lysis module and containing a solid phase comprising covalently immobilized capture probes that are capable of capturing 80% of human genomic DNA;
    a thermocycling module within the housing coupled to the purification module and capable of containing a polymerase chain reaction;
    a fragmentation module within the housing coupled to the thermocycling module; and
    a microarray module within the housing coupled to the fragmentation module and capable of holding the microarray and a liquid in contact with the microarray;
inserting the microarray into the microarray port;
inserting the sample through the sample port and into the lysis module; and
coupling the apparatus to a device, the device performing a process comprising:

sonicating the sample in the lysis module;
pumping the product of the sonication into the purification module;
hybridizing 80% of the human genomic DNA in the product of the sonication to the capture probes to produce a purified product;
pumping the purified product to the thermocycling module;
introducing a set of PCR primers into the thermocycling module;
performing a polymerase chain reaction within the thermocycling module to produce a product of the polymerase chain reaction containing PCR-produced oligonucleotides;
pumping the product of the polymerase chain reaction into the fragmentation module;
introducing a restriction enzyme into the fragmentation module;
heating the contents of the fragmentation module to cause fragmentation of the PCR-produced oligonucleotides to produce fragmented oligonucleotides;
pumping the product of the fragmentation into the microarray module;
circulating the product of the fragmentation over the microarray to allow hybridization of the fragmented oligonucleotides to the probes on the microarray; and
performing one or more washing or staining steps on the hybridized microarray.

9. The method of claim 8, further comprising:
mixing the sample with a lysis reagent.

10. The method of claim 8, further comprising:
performing a reverse transcriptase reaction in the thermocycling module before performing the polymerase chain reaction.

11. The method of claim 8, further comprising:
biotinylating the product of the fragmentation.

12. The method of claim 8, further comprising:
removing the apparatus from the device; and
coupling a second instance of the apparatus to the device.

* * * * *